US00PP11631P

United States Patent [19]

Fear et al.

[11] Patent Number: Plant 11,631

[45] Date of Patent: Nov. 14, 2000

[54] PEACH TREE NAMED 'SUPECHSIX'

[75] Inventors: Carlos D. Fear, Aptos; Bruce D. Mowrey, La Selva Beach; David W. Cain, Bakersfield, all of Calif.

[73] Assignee: Sun World International, Inc., Bakersfield, Calif.

[21] Appl. No.: 09/007,371

[22] Filed: Jan. 15, 1998

[51] Int. Cl.[7] ..... A01H 5/00

[52] U.S. Cl. ..... Plt./197

[58] Field of Search ..... Plt./197

[56] References Cited

U.S. PATENT DOCUMENTS

| | | | |
|---|---|---|---|
| P.P. 4,917 | 11/1982 | Zaiger | Plt./197 |
| P.P. 5,463 | 5/1985 | Zaiger | Plt./197 |
| P.P. 6,025 | 9/1987 | Balakian | Plt./198 |

*Primary Examiner*—Howard J. Locker
*Assistant Examiner*—Wendy A. Baker
*Attorney, Agent, or Firm*—Knobbe, Martens, Olson & Bear, LLP

[57] ABSTRACT

A new and distinct variety of peach tree characterized by its very early ripening fruit which has a round shape, an indented stylar tip, and a high (70–100%) percentage of red coloration.

2 Drawing Sheets

BACKGROUND AND SUMMARY OF THE INVENTION

This invention relates to the discovery and asexual propagation of a new variety of hybrid peach tree, *Prunus persica* cv. Supechsix. The tree is a very early ripening commercial peach variety for market use. It arose in a controlled cross made by Carlos D. Fear, was first selected by Bruce D. Mowrey, was evaluated by Bruce D. Mowrey and David W. Cain, and was asexually propagated by Bruce D. Mowrey. Its seed parent is Flordaprince (unpatented), and its pollen parent is Queencrest®, which is the subject of U.S. Plant Pat. No. 6025.

The new peach tree variety cv. Supechsix may be distinguished from other presently available peach cultivars, particularly the Goldcrest cultivar (unpatented), by the following combination of characteristics: its larger size, a greater percentage of desirable red coloration (70–100% vs. 70–90%), a more round shape with an indented stylar tip rather than a slight pointed tip, and a lower winter chilling requirement of approximately 400 hours below 45° F. vs. 650 hours for Goldcrest. The new variety holds these distinguishing characteristics through succeeding asexual propagations by budding, which propagations were carried out in the vicinity of Wasco, Kern County, Calif.

Among the characteristics which distinguish the new variety of peach tree from its pollen parent, Queencrest®, are the following: the new variety ripens approximately 15 days before Queencrest® and it has a lower winter chilling requirement of about 400 hours vs 600 hours for Queencrest®. It also has a more desirable round shape and has an indented stylar tip as opposed to the pointed tip of Queencrest®, which can be damaged during harvest and shipping. It has a higher (70–100%) distribution of desirable red coloration as compared to Queencrest® (50–80%). The extent of blush varies depending on the degree of exposure to sunlight.

The new variety may be distinguished from its seed parent, Flordaprince in the following characteristics: it has a higher winter chilling requirement of approximately 400 hours of temperature below 45° F. vs 150 hours for Flordaprince. It also ripens approximately 12–15 days before Flordaprince and has a more round and less blocky shape. Further, Supechsix has more (70–100%) external red blush than Flordaprince (50–80%) and is firmer and has better shipping and storage ability than Flordaprince. The instant variety has been successfully stored in non-atmospherically controlled storage at 32° to 38° F. for up to 20 days. It has been successfully transported via commercial refrigerated trucks over distances in excess of 2000 miles.

The new variety may be distinguished from the peach tree variety described in U.S. Plant Pat. No. 4917 by having different parents, being not heterozygous for the nectarine trait, by having acid levels characterized as standard or normal type as opposed to subacid as described for U.S. Plant Pat. No. 4,917, and by ripening approximately two to three weeks earlier than U.S. Plant Pat, No. 4,917.

The Supechsix variety may be distinguished from the peach variety Stark Gulf Queen™ (U.S. Plant Pat. No. 5,463) by having different parent, not being heterozygous for the nectarine trait, and by ripening approximately thirty days earlier than Stark Gulf Queen™ when grown in the San Joaquin valley of California (late April as opposed to early June).

BRIEF DESCRIPTION OF THE FIGURES

FIG. 1 illustrates, in full color, a typical stem and mature leaves of the peach tree and the ripe fruit as viewed from the stem and in profile. The drawing also illustrates the fruit sectioned in half from end to end, one-half of the fruit shown with the stone in place in the flesh.

Figure 2:
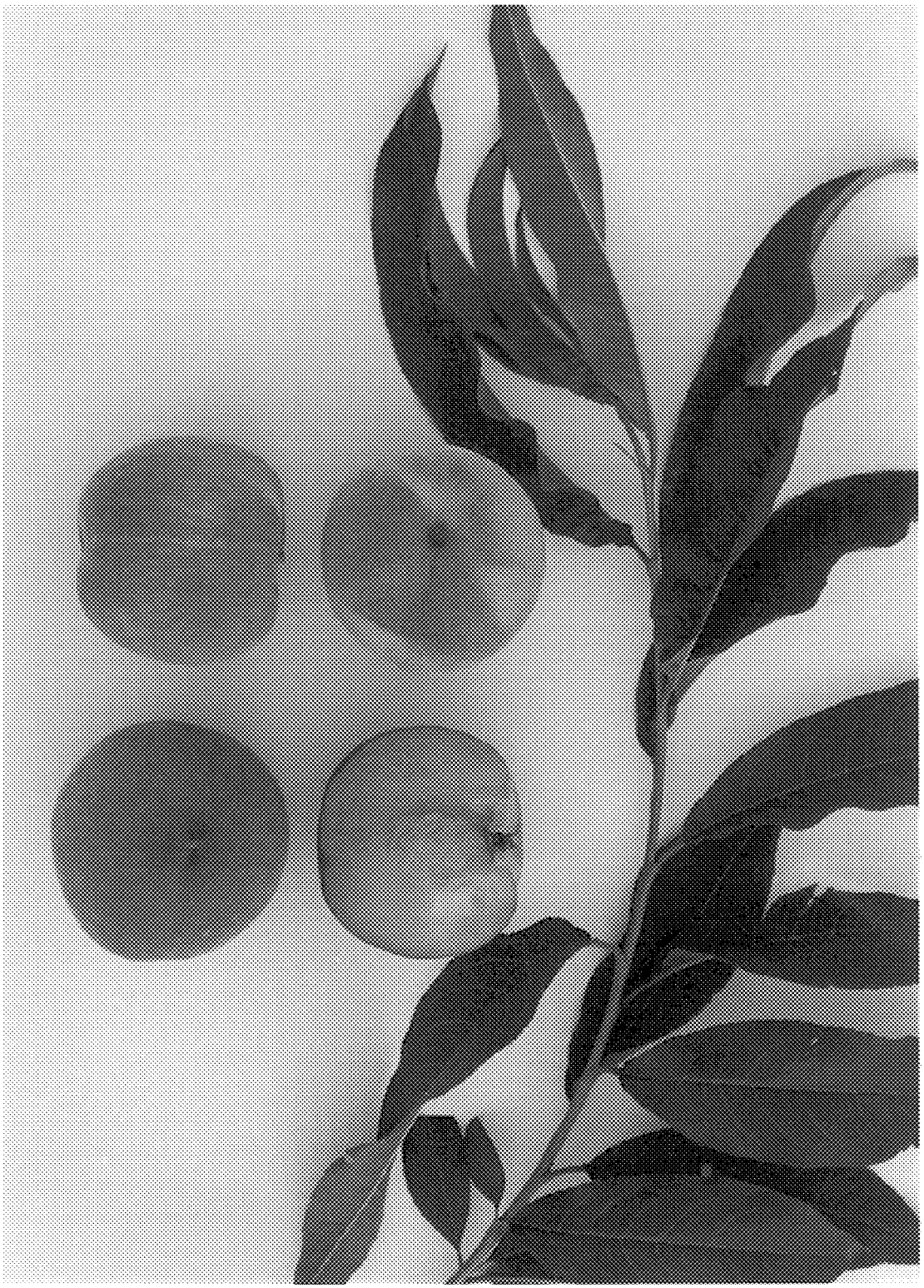
FIG. 2 illustrates, in full color, a comparison of the stage of bloom between Supechsix and its pollen parent, Queencrest®. Two representative stems of Supechsix are shown on the left, and two representative stems of Queencrest® are shown on the right.
Figure 2:
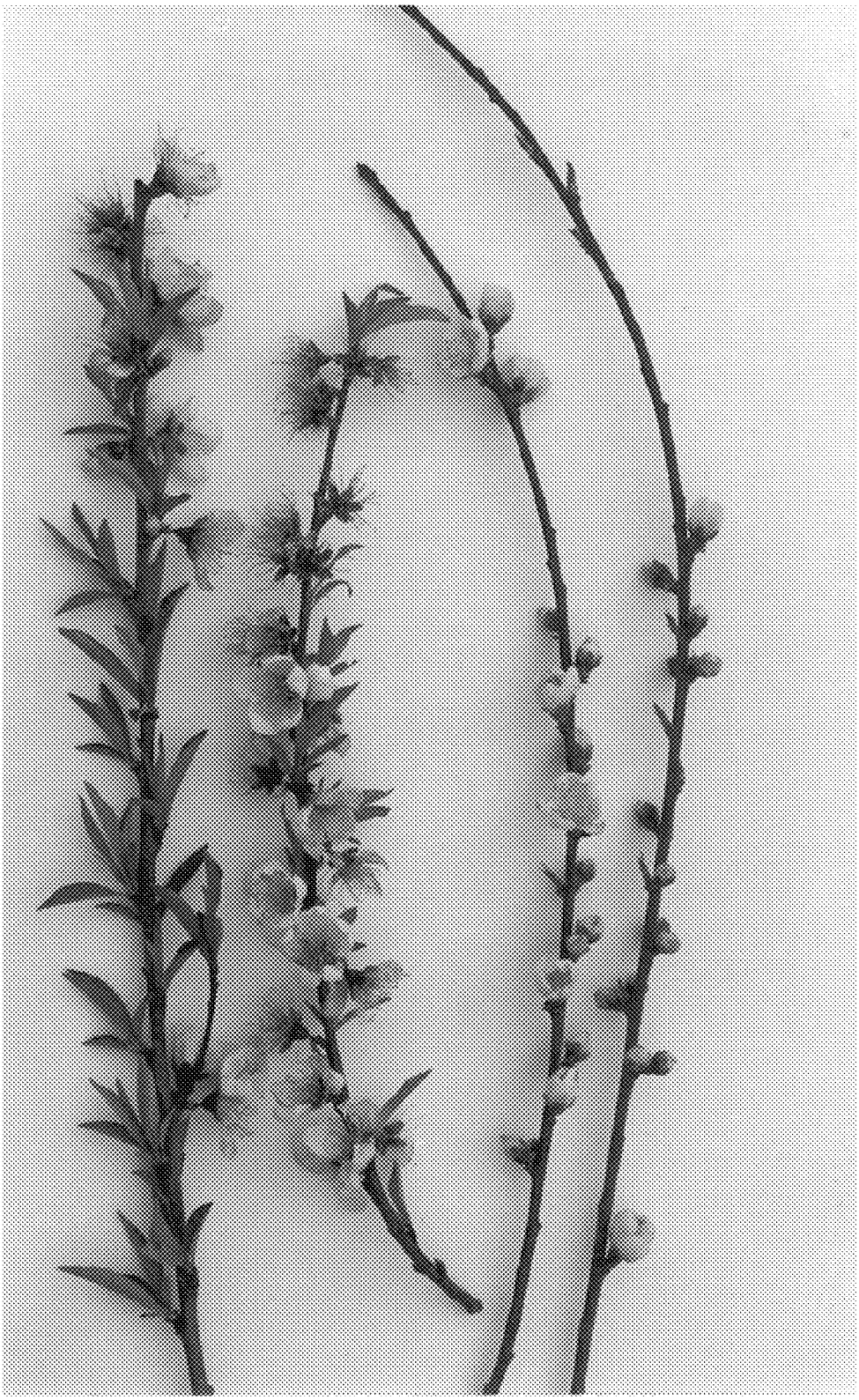

The colors illustrated in the FIGURES are as accurate as reasonably possible to attain in color photographic reproductions of this type.

DETAILED BOTANICAL DESCRIPTION OF THE INVENTION

Throughout this specification, color names beginning with a small letter signify that the name of that color, are used in common speech, is aptly descriptive. Color names with capital letters designate values based upon the R.H.S, Colour Chart, published by The Royal Horticultural Society, London.

The descriptive matter which follows pertains to peach trees of the new variety grafted onto Nemared root stock and grown in the vicinity of Wasco, Kern County, Calif. during 1996 and is believed to apply to plants grown under similar conditions of soil and climate elsewhere. Such trees were four years old, and were maintained at height of about 10 feet and a crown diameter of about 10 feet by annual prunings.

Tree

When budded on Nemared root stock the tree is of medium size and medium vigor typical of most commercial peach varieties grown in California. Trees typically produce about 72.5 cm long lateral shoots when grown using normal commercial practices. It is semi-upright in habit and vase-formed in shape. The foliage is of medium density. The trees are hardy, regular bearers and medium productive.

The trunk is round in outline and of medium circumference, averaging 28.4 inches at 1 foot above ground level on 7-year old trees. Surface texture is medium and smooth exhibiting slight exfoliation of the bark. The branches are likewise round in outline and average 10.7 inches in circumference on 7-year-old trees as measured 1 foot from the trunk juncture with the branch. Surface texture is medium smooth with a dull surface apperance. Trunks and branches are about Grey-Brown 199B in color. Lenticles are few and large, averaging about 4.3 cm long with an average density of 1.6 lenticles per square centimeter. The tree is productive for an early season peach, producing about 110 pounds of fruit per tree.

Leaves

In general, leaves are of a large size, having an average length of about 16,6 cm and an average width of about 4.3 cm. Leaves are lanceolate in outline and upfolded in profile. Leave blade tips curve downwardly at an acute angle. The leaf margin is finely serrate, and is slightly undulated. The leaf is cuspidate at the apex, V-shaped at the base, and medium in thickness. The upper surface of the leaf is about Yellow-Green 147A in color, and of medium glossiness. The upper leaf surface is smooth with a semi-glossy appearance; pubescence is absent. The lower leaf is about Yellow-Green 147B in color, and weak in glossiness. Pubescence is absent from the lower surface, which has a smooth texture and a dull appearance.

The petiole is of medium length and medium thickness. There is an average of 2.2 small, globose glands alternately positioned on both the leaf base and the petiole. Stipules fall off.

Wood (leaf) buds are medium in size and ovoid in shape. Their position, relative to the shoot, is adpressed. Their support is said and not decurrent. The time of bud burst is early.

On flowering shoots anthocyanin coloration is present in medium intensity. The shoots are of medium size and thickness, about 5.5 mm. Internode length is medium, about 2.8 cm. Buds are of average density and are isolated in groups of two or more on one-year-old shoots. The ratio of wood (leaf) buds to flowering shoots is about 1/2.5.

Flowers

Flowers buds are, in general, hardy, of medium size and length, plump, and freely positioned. Buds are pubescent and about Greyed-Orange 165A in color.

Flowers bloom early, and attain full bloom by about February 19 in Wasco, Kern County, Calif. Blooms have a duration of about 10 days. The fully opened flower is large, about 3.7 cm, and is of rosaceous shape with overlapping petals. The fully opened flower is about Red-Purple 65D in color. The peduncle is short in length and medium in thickness; pubescence is absent.

The receptacle is of medium depth. Pubescence is present on the inner surface at the white bud stage. Pubescence is, however, absent from the outer surface.

Sepals are adpressed to petals and ovate in shape, with no pubescence on the inner surface and pubescence present on the outer surface.

Petals are large in size, about 46 mm wide, transverse broad elliptic in shape, have short claw length, medium margin waviness, and a medium base angle. The division of the upper margins is entire, and pubescence is absent on both inner and outer surfaces.

The stigma is above the anthers. The anthers are about Red 43C in color just before dehiscence. Pollen is about Yellow-Orange 14D in color. Stamens are perigynously positioned. The number of pistils is always one; no supplementary pistils have been observed. The ovary and style are both pubescent, displaying dense hairs.

Fruit

The fruit, as described, was firm at maturity on April 29. The fruit at firm ripe maturity is small, weighing on average 112.9 g, and having an axial diameter of 5.0 cm and a transverse diameter in the suture plane of 6.4 cm. At right angles to the suture plane, the diameter is about 6.2 cm, thus indicating a uniform, globose shape. The position of the maximum diameter is towards the middle of the fruit. The fruit is symmetric about the suture line. The fruit ripens very early with normal commercial harvest occurring between April 29 and May 11.

The fruit is for market use and has a medium keeping quality and good shipping quality. It exhibits good resistance to insects and diseases when grown under commercial conditions in Kern County, Calif.

The suture is an inconspicuous line. The ventral surface is rounded slightly with equal lips. The apex is distinctly depressed, and exhibits pubescence of medium density. The pistil base does not persist.

The stem cavity is circular, with the suture showing on one side. The depth of the cavity is about 1.3 cm, and its width is about 2.7 cm. The base of the fruit is rounded. The apex is slightly depressed in shape and the pistil point is oblique in shape.

The stem is about 0.8 cm in length, stout, glabrous, and adheres strongly to the stone. The skin, which is of medium thickness and texture, is tenacious to the flesh, and is without roughness or reticulation. The skin shows no tendency to crack in dry season. Ground color of the skin is about Yellow 11B; blush color of the skin is about Red 53B. Down is abundant and rolls up when rubbed.

The color of the flesh of firm, ripe fruit is about Yellow-Orange 19A surrounding the pit cavity and the pit cavity is about Yellow 11B in color. Slight red coloration about Red 39A may develop in soft, ripe fruit. Amygdalin is wanting and juice is moderate. The flesh has a low to medium sugar content. Flesh texture is medium coarse and melting, with abundant coarse fibers. Fruit ripens earliest at the apex, and is of fair to good eating quality. The flavor and aroma are delicate, typical of an early season peach.

The stone clings, adhering to the flesh over its entire surface. Due to this variety's very early ripening characteristics, the stone is physiologically immature and is not fully lignified when the fruit is ripe. Fibers of the stone are long. The stone is medium in size, being about 3.1 cm in length, 2.1 cm in breadth, and having a stalk end of about 0.4 cm. The angle of the stalk end is obtuse. The form of the stone in profile is generally oval. The form in ventral view is globular. The stone's base is slightly oblique, its apex is rounded and its hilum is oval in shape. The position of the stone's maximum breadth is toward the middle and the sides are generally equal. The surface of the stone is regularly furrowed near the base and is pitted throughout. There is a partly developed outgrowing keel. The ridges are rounded towards the base and the pits are elongated. The ventral edge of the stone is thin with a wing toward the base and the dorsal edge is narrow with shallow grooves throughout, The color of the stone is about Greyed-Orange 165D. The stone has a moderate tendency to split.

What is claimed is:

1. A new variety of peach tree cv. Supechsix, as illustrated and described herein.

* * * * *